United States Patent
Godbole et al.

(10) Patent No.: US 6,326,508 B1
(45) Date of Patent: Dec. 4, 2001

(54) PURIFICATION AND RECOVERY OF ACETONITRILE

(75) Inventors: Sanjay Purushottam Godbole, Solon, OH (US); Richard Lee Wappelhorst, Port Lavaca, TX (US); Paul Alan Jacobson, Brecksville, OH (US)

(73) Assignee: The Standard Oil Company, Chicago, IL (US)

( * ) Notice: Subject to any disclaimer, the term of this patent is extended or adjusted under 35 U.S.C. 154(b) by 0 days.

(21) Appl. No.: 09/654,631

(22) Filed: Sep. 5, 2000

Related U.S. Application Data

(63) Continuation of application No. 09/027,864, filed on Feb. 23, 1998, now abandoned.

(51) Int. Cl.$^7$ ................................................ C07C 255/00
(52) U.S. Cl. .............................................................. 558/441
(58) Field of Search ............................... 558/441; 203/623

(56) References Cited

U.S. PATENT DOCUMENTS 4,362,603 * 12/1982 Presson et al. ...................... 558/441

* cited by examiner

*Primary Examiner*—Joseph K. McKane
*Assistant Examiner*—Joseph Murray
(74) *Attorney, Agent, or Firm*—Thomas E. Nemo; Patrick J. Kim

(57) ABSTRACT

The method of the present invention comprises feeding crude acetonitrile containing acrylonitrile as an impurity and water into the upper portion of a distillation column, distilling the crude acetonitrile in the presence of the water for a time sufficient to allow substantially all of the acrylonitrile impurity to be vaporized in the presence of the water, removing substantially all of the acrylonitrile in an overhead stream exiting from the distillation column and recovering the crude acetonitrile substantially free of acrylonitrile impurity from the lower portion of the distillation column. In particular, the method can be utilized to produce HPLC grade acetonitrile (UV cutoff <190).

16 Claims, 1 Drawing Sheet

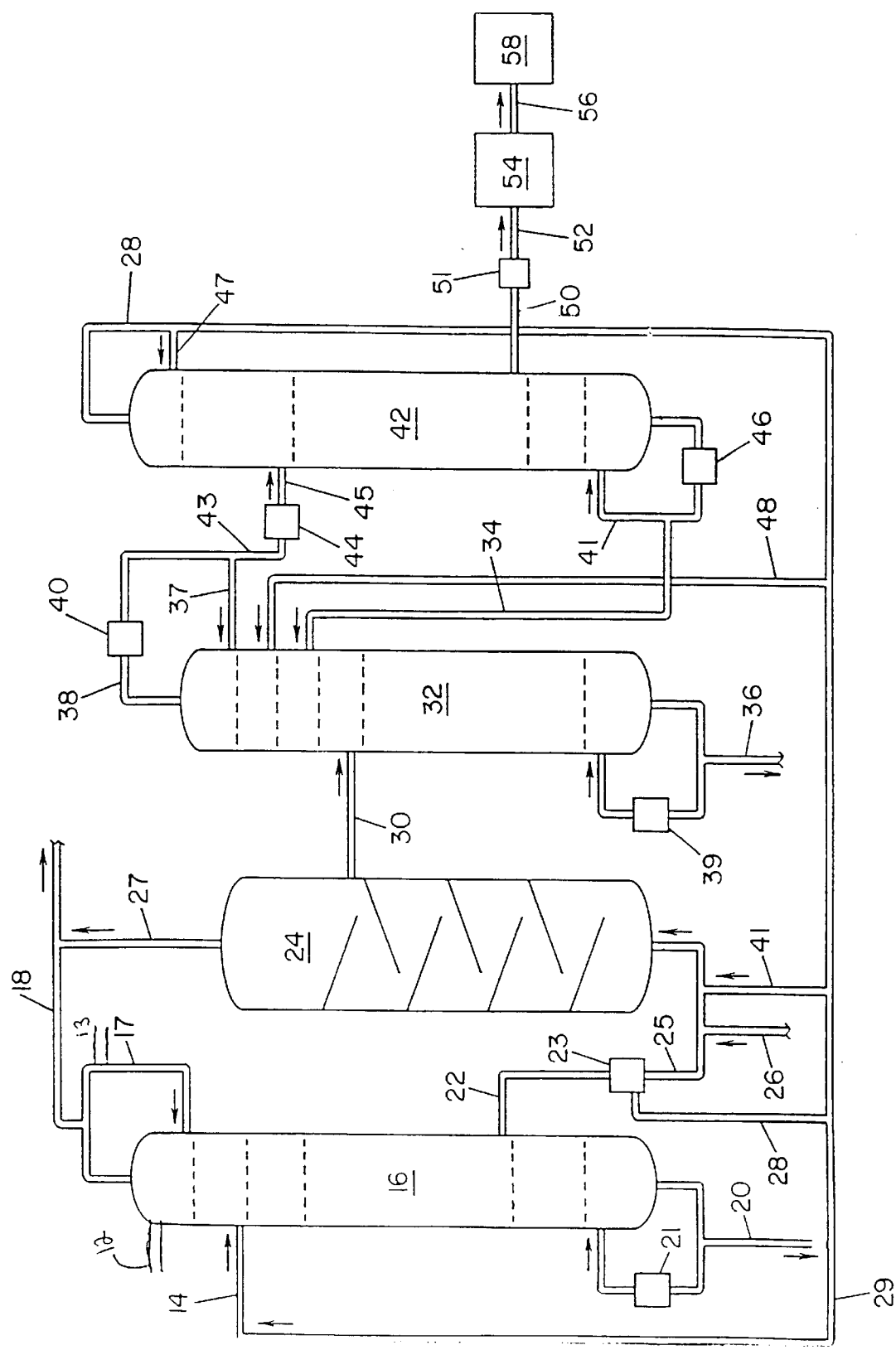

PURIFICATION AND RECOVERY OF ACETONITRILE

This is a continuation, of application Ser. No. 09/027,864 filed Feb. 23, 1998 now abandoned.

BACKGROUND OF THE INVENTION

Field of the Invention

In the production of acrylonitrile by the catalytic ammoxidation of propylene with ammonia and oxygen, a crude acetonitrile co-product is produced. The term "crude acetonitrile" means liquid acetonitrile containing hydrogen cyanide, water and other impurities. The other impurities may include acrylonitrile, acetaldehyde, acetone, methanol, acrolein, oxazole, cisand trans-crotononitrile, methacrylonitrile and allyl alcohol. The relative proportions of the components of the crude acetonitrile can vary over a wide range depending on various conditions. The concentration level of the organic impurities in the crude acetonitrile is usually less than 15% with no single organic component found in greater than 2 to 4 wt % concentration. Usually crude acetonitrile obtained from an acrylonitrile plant contains between 25 and 85% acetonitrile. Typically, the crude acetonitrile is composed on a weight basis of 52% acetonitrile, 43.6% water, 2.5% hydrogen cyanide, 0.5% acrylonitrile and 1.3% other organic impurities as mentioned above. Originally, during the manufacture of acrylonitrile, the crude acetonitrile produced was disposed of by incineration. However, in recent years, this material has been recovered and purified and sold to add value to the process.

There are two basic technologies for the "first stage" purification of crude acetonitrile co-product produced during the manufacture of acrylonitrile. These processes typically produce acetonitrile of sufficient purity for use as a bulk solvent. The first and most common practiced technology is a batch process. In this process, crude acetonitrile is distilled to remove the bulk of the HCN as a low boiling distillate. The remaining material is allowed to react either with a mixture of strong base, usually an aqueous sodium hydroxide solution and formaldehyde and water, or with a strong base and ferrous sulfate, to remove essentially all the remaining HCN. (See U.S. Pat. Nos. 4,328,075 and 3,201, 451.) The HCN free material is then distilled to produce an acetonitrile/water azeotrope containing about 25% water. The azeotrope is then slurried with anhydrous calcium chloride to remove the bulk of the water in the azeotrope and produce an acetonitrile/water mixture containing about 3 to 5% water. This mixture is then distilled to produce acetonitrile product having an acceptable purity for many uses. Typically, this material contains several parts per million by weight of acrylonitrile or other impurities which absorb strongly in the UV spectrum.

The second method of producing "first stage" purified acetonitrile is a continuous recovery process which involves (1) first distilling crude acetonitrile in a distillation zone at a pressure of at or above 1 atmosphere to remove the bulk of the HCN, (2) passing this azeotrope through a digester in which the remaining HCN is removed by treatment with an aqueous solution of base and formaldehyde, (3) performing a second distillation at a pressure less than 1 atmosphere to separate the material into a bottoms product containing water and a second acetonitrile/water azeotrope with higher acetonitrile concentration, and (4) a third distillation at a pressure above the pressure of the first distillation to produce purified acetonitrile as a side stream. This process is described in U.S. Pat. No. 4,362,603 assigned to the assignee of the present invention and herein incorporated by reference. Acetonitrile purified by this method can contain up to several parts per million by weight of acrylonitrile, acetamide, oxazole, or other UV-absorbing impurities.

While these two basic procedures for forming bulk solvent grade acetonitrile are widely accepted, their use in producing acetonitrile for chromatographic applications is not acceptable because the acetonitrile contains a relatively high amount of UV-absorbing impurities. There is a distinct market for high performance (HPLC grade) acetonitrile essentially free of UV-absorbing impurities (UV cutoff for impurities of <190nm).

The specifications for HPLC grade acetonitrile render the material produced by first stage purification unacceptable, therefore requiring further processing by producers of HPLC grade acetonitrile. The traditional commercial methods of acetonitrile purification to achieve this high grade of purity utilize costly multi-step processes involving, for example, permanganate oxidation, acid treatment, phosphorous pentoxide drying and two distillations.

More recent procedures disclosed in U.S. Pat. Nos. 5,292, 919 and 5,426,208 disclose treatment of acetonitrile with ozone followed by passing the acetonitrile through a series of adsorbent beds of charcoal or graphitized carbon, activated alumina, and/or molecular sieves.

Several other patents and literature articles describe the purification of acetonitrile with acidic ion exchange resins for removal of impurities from acetonitrie. British Patent 1,223,915 describes the use of a series of strong acid cation exchange resins for the reduction of the concentration of bases, ammonia and 3,3'-iminodipropionitrile, in aqueous acetonitrile from 500 ppm each to 10 ppm and <50 ppm, respectively. This level of purity is still not acceptable for HPLC grade acetonitrile.

The process of the present invention is directed to an improved procedure for easily removing substantially all of the acrylonitrile impurity present in crude acetonitrile, in particular, crude acetonitrile produced as a co-product during the manufacture of acrylonitrile. In addition, the process of the present invention results in the production of a crude acetonitrile intermediate stream which simplifies the process for producing HPLC grade acetonitrile resulting in substantial economic savings.

SUMMARY OF THE INVENTION

It is a primary object of the present invention to provide an improved process for the substantial removal of acrylonitrile impurity present in crude acetonitrile.

It is a further object of the present invention to provide an improved process for the substantial removal of acrylonitrile impurity present in crude acetonitrile obtained as a coproduct during the manufacture of acrylonitrile.

It is a still further object of the present invention to provide an improved process for the production of HPLC grade acetonitrile.

It is another object of the present invention to provide an improved recovery efficiency and product recycle process for the production of solvent grade acetonitrile.

Additional objects, advantages and novel features of the invention will be set forth in part in the description which follows, and in part will become apparent to those skilled in the art upon examination of the following or may be learned by the practice of the invention. The objects and advantages of the invention may be realized and obtained by means of the instrumentalities and combinations particularly pointed out in the appended claims.

To achieve the foregoing objects in accordance with the purpose of the present invention as embodied and described therein, the method of the present invention comprises feeding crude acetonitrile containing acrylonitrile as an impurity and water into the upper portion of a distillation column, distilling the crude acetonitrile in the presence of the water for a time sufficient to allow substantially all of the acrylonitrile impurity to be transferred to the vapor phase by the water and, therefore, removed in an overhead stream exiting from the distillation column and recovering the crude acetonitrile substantially free of acrylonitrile impurity from the lower portion of the distillation column.

In a preferred embodiment of the process of the present invention the water is fed to the distillation column above the point where the crude acetonitrile enters the distillation column.

In a further preferred embodiment of the process of the present invention the distillation tower is equipped with trays and the water is fed into the distillation column at a point above the highest tray present in the column.

In a further preferred embodiment of the process of the present invention the distillation tower is equipped with packing.

In a still further preferred embodiment of the process of the present invention the light ends column top distillation temperature is between about 140° F. to 160° F. (preferably 144° F. to 155° F., especially preferred being 148° F. to 152° F.) at a pressure of about 18 psia.

The process of the present invention enables one to produce acetonitrile recovered from the light ends distillation column side stream which has substantially reduced acrylonitrile impurity levels compared to previously recovered light ends distillation column side stream acetonitrile. For example, during the practice of the process of the present invention the acrylonitrile impurity level of the recovered side stream acetonitrile is reduced from about 240 ppm to about 40 ppm which represents a reduction of about 600% from the amount of acrylonitrile impurity present in typical light ends column side stream crude. While practicing the process of the present invention the solvent grade acetonitrile product obtained from the product column sidestream is decreased from a range of about 1 to 3 ppm to a value below detection limits of 100 ppb.

It has further been discovered that the practice of the process of the present invention results in a substantial economic advantage when practice in conjunction with the subsequent procedure of producing HPLC grade acetonitrile. Since the practice of the present invention results in the production of a solvent grade acetonitrile product which contains no detectable acrylonitrile compared with typical solvent grade acetonitrile obtained from the distillation procedures of the prior process, it has been found that substantially less caustic (e.g. 60% to 70%) and almost no formaldehyde have to be added during the downstream treatment of the solvent grade acetonitrile to produce HPLC grade acetonitrile. In fact, compared to HPLC caustic treatments required in the previous processes the decrease in the caustic usage is almost 80% to 85% resulting in digester operation simplification, less polymerization related operational problems and and substantial cost savings in the overall purification process.

The details of the preferred production process for the manufacture of HPLC grade acetonitrile have been set forth in detail in copending U.S. Ser. No. 08/632,382 filed Apr. 10, 1996 assigned to the assignee of the instant application and herein incorporated by reference.

In accordance with another purpose of the present invention as embodied and described herein, the method of the present invention comprises (1) feeding crude acetonitrile containing acrylonitrile as an impurity and water into the upper portion of a first distillation column affixed with a first overhead reflux loop at a first pressure of at least 1 atmosphere and distilling the crude acetonitrile in the presence of the water for a time sufficient to allow substantially all of the acrylonitrile impurity to be vaporized in the presence of water and removed along with HCN impurity present in the crude acetonitrile in an overhead stream exiting from the first distillation column producing a first acetonitrile/water azeotrope substantially free of acrylonitrile impurity and a first bottom product containing water and a first bottom product containing water, (2) distilling the first azeotrope in a second distillation column affixed with a second overhead reflux loop at a second pressure less than 1 atmosphere to separate the first azeotrope into a second bottoms product containing water and a second acetonitrile/water azeotrope having a greater acetonitrile concentration than the first azeotrope, (3) distilling the second acetonitrile/water azeotrope in a third distillation column affixed with a third overhead reflux loop at a third pressure above 1 atmosphere to produce a third acetonitrile/water azeotrope containing substantially all of the water from the second azeotrope. A third bottoms product comprising acetonitrile and heavy organics, and a side stream comprising highly pure acetonitrile, and (4) passing the highly pure acetonitrile side stream through an acidic ion exchange resin to further purify said highly pure acetonitrile producing HPLC grade acetonitrile wherein the reflux ratios in Steps 1, 2 and 3 are kept at greater than 2.7 to 1, greater than 2.2 to 1 and greater than 3.0 to 1, respectively.

The term "reflux ratio" as used above is defined as follows: for the first column (light ends column), the reflux ratio is defined as the ratio of overhead reflux flow rate divided by the rate of feed from the column side to the digester. For the second distillation (drying column), the reflux ratio is defined as the ratio of overhead reflux flow rate to the rate of the overhead draw-off to the product column. For the third distillation column (product column), the reflux ratio is defined as the ratio of overhead reflux flow rate to the rate of acetonitrile product side stream flow.

In a preferred embodiment of the present invention the light ends column reflux ratio is preferably greater than 4.4 to 1, the drying column reflux ratio is preferably greater than 4.5 to 1 and the product column reflux ratio is preferably greater than 8.0 to 1. Especially preferred is a light ends column reflux ratio of greater than 5.2 to 1, a drying column reflux ratio of greater than 5.0 to 1 and a product column reflux ratio of greater than 10.9 to 1.

The acidic ion exchange resins are used in their $H^+$ form. Regeneration of resin beds can be carried out by passing sulfuric acid or hydrochloric acid solutions over the resin beds by any conventional procedure known to the art. After regeneration, the resin bed is washed with several bed volumes of acetonitrile to dry the bed and remove impurities.

The resin treatment step can be carried out in any mode known in the art. The resin treatment step can be carried out preferably as a continuous fixed bed process, although slurry mode operation in (optionally) stirred tank reactors, for example, is within the scope of this invention. The adsorbent beds can be operated in a continuous mode at ambient temperature or at elevated or reduced temperature as required, and with either upward or downward flow, with temperatures from 15 to 35° C. being preferred. A flow rate ranging from about 0.1 to 300 bed volumes per hour is within the scope of the process of the present invention, although operating outside this range is also satisfactory. Preferably, flow rates are in the range of 0.2 to 50 bed volumes per hour. Most preferably, from 0.5 to 35 bed volumes per hour.

Lastly, a final distillation of the HPLC grade acetonitrile is optional and may be carried out by conventional means known in the art. Preferably, means of distillation are distillation in glass or stainless steel equipment, although other materials of construction inert to acetonitrile and free of contaminants are within the scope of the invention. Fractionation can be accomplished with Oldershaw columns, or columns packed with beds, helices, trays, turnings, saddles, or other conventional packing material known in the art.

Suitable ion exchange resins useful in the practice of the present invention include strong acid type incorporating sulfonic acid functional groups, either gel form or macroreticular or macroporous form. Examples include, but are not restricted to, Amberlyst 15, Amberlyst XN 1010, Dowex 50, Amberlite IRP-69, Amberlite IR-118, and their equivalents. Also acceptable but less preferred are the so-called weak acid resins incorporating carboxylic acid functional groups, either gel form or macroreticular or macroporous form. Examples of this class of resin include, but are not restricted to, Amberlite IRP-64 and IRC-50S. Particularly preferred are the strong acid resins specifically designed for non-aqueous applications, such as Amberlyst 15.

BRIEF DESCRIPTION OF THE DRAWING

The FIGURE is a flow diagram of the practice of the process of the present invention.

DETAILED DESCRIPTION OF THE INVENTION

In accordance with the process of the present invention crude acetonitrile containing acrylonitrile as an impurity and water are fed into the upper portion of a distillation column. The crude acetonitrile is then distilled in the presence of the water for a time sufficient to allow substantially all of the acrylonitrile impurity present in the crude acetonitrile to be vaporized in the presence of the water and removed in an overhead stream exiting from the distillation column. The crude acetonitrile substantially free of acrylonitrile impurity is recovered from the lower portion of the distillation column preferably as a side stream.

In another aspect of the practice of the present invention the crude acetonitrile substantially free of acrylonitrile impurity is further processed to recover highly pure acetonitrile. By "highly pure" acetonitrile is meant High Performance Liquid Chromatography (HPLC) grade acetonitrile, acetonitrile of extremely high purity and being sufficiently free of UV absorbing impurities (well below 0.1 to 0.3 ppm max) having a UV absorbance cut off of <190 nm. The crude acetonitrile which is processed in accordance with the present invention is any acetonitrile/water mixture containing at least 15% water. Thus, the inventive process is applicable in the processing of various water/acetonitrile azeotropes. The invention, however, finds broadest application in the processing of the crude acetonitrile streams produced by the ammoxidation of propylene with oxygen and ammonia to form acrylonitrile. As indicated above, such crude acetonitrile streams normally contain about 52% acetonitrile, 43.6% water, 0.5% acrylonitrile, 2.5% HCN and 1.3% other minor impurities such as oxazole, allyl alcohol, acetone and propionitrile.

Crude acetonitrile recovered from an acrylonitrile plant and having the above composition can be conveniently processed by the present invention. Reference will now be made in detail in accordance with the process flow scheme illustrated in the Figure to the process of the present invention as it applies to the manufacture of HPLC grade acteonitrile.

In accordance with this preferred system, crude acetonitrile via inlet line 14 and water via inlet line 12 ,or optionally via line 13, are fed into light ends column 16 wherein the crude acetonitrile containing acrylonitrile as an impurity are distilled at a temperature of between about 140° F. to 160° F. (preferably 144° F. to 155° F., especially preferred being 148° F. to 152° F.) at a pressure of about 18 psia for a sufficient time to allow a substantial amount of the acrylonitrile impurity to be vaporized by extractive distillation and removed from the column via line 18. The light impurities in the crude acetonitrile, namely HCN, oxazole and acetone, are also withdrawn from light ends column 16 as a vapor draw via line 18 and are condensed along with the acrylonitrile and refluxed back into the upper region of column 16 via reflux line 17. Preferably, the reflux ratio as defined above is greater than 2.7:1. Unrecovered overheads are removed via line 18 and transported to vent scrubbers (not shown) or any other conventional means for waste treatment. Water is recovered from the bottom of light ends column 16 and discharged via line 20 to waste treatment with partial recycle through reboiler 21. A first acetonitrile/water azeotrope containing about 70% acetonitrile, 30% water, 500 ppm HCN, acrylonitrile in the range of 40 ppm to 60 ppm and very small amounts of heavy organics is recovered via line 22 as a vapor side draw condensed in condenser 23 and transported via line 25 to digester 24.

An HCN digester composition comprising an aqueous solution of sodium hydroxide and formaldehyde is added via line 26 to digester 24 so that any remaining HCN and acrylonitrile in the first azeotrope is destroyed. As mentioned above, the amount of caustic and formaldehyde additives required is substantially reduced in the practice of the process of the invention and, in fact, in the optimum practice of the process of the present invention it is envisioned that the use of formaldehyde can even be eliminated.

The HCN-acrylonitrile free acetonitrile/heavy organics and water mixture passing out of digester 24 is charged via line 30 into drying column 32 and unrecovered material is removed from digester 24 as overheads via line 27 and combined in line 18 for transport to vent scrubber and waste treatment. In addition, a stream comprising acetonitrile containing a small amount of heavy impurities is also charged into drying column 32 via line 34 from product column 42. In drying column 32, the acetonitrile/heavy organics and water mixture is distilled at a pressure below one atmosphere, e.g. 3.4 psi and heavy organics are discharged for waste treatment via line 36 with some recycled back via reboiler 39 into the bottom of column 32, and a gaseous top draw comprising a second acetonitrile/water azeotrope, the second azeotrope containing about 10% water, is removed from column 32 via line 38. At least part of this second azeotrope is condensed through condenser 40 and refluxed back into column 32 via reflux line 37. The reflux ratio in this step as defined above is greater than 2.2:1.

The second acetonitrile/water azeotrope is charged via line 38 into condenser 40 where it is condensed, passed via line 43 through heat exchanger 44 where it is heated, and then charged via line 45 into product column 42. In product column 42, the second acetonitrile/water azeotrope is distilled at high pressure, e.g. 50 psia. A bottoms product comprising acetonitrile containing heavy impurities is withdrawn from the bottom of product column 42 into reboiler 46 for partial recycling to column 42 via line 41 and drying column 32 via line 34. A third acetonitrile/water azeotrope is withdrawn from the top of product column 42 via line 28 and condensed and recycled as reflux back to the top of product column 42 via reflux line 47. The uncondensed vapors continue via line 28 to the azeotrope condenser 23 where they are mixed with the first azeotrope. Alternatively, these uncondensed vapors may be rerouted to light ends column 16 via lines 29 and 14. Preferably, the reflux ratio as defined above of greater than 3.0:1 for this step of the process. In an alternative embodiment of the present invention, some liquid from product column overhead stream 28 may be recycled to drying column 32 via line 48 or digester 24 via line 41. Because product column 42 is operated at high pressure, all of the water in the second acetonitrile/water azeotrope charged into product column 42 is recovered in the overhead stream of product column 42, i.e. the third acetonitrile/water azeotrope, leaving high purity acetonitrile in the product column. This high purity acetonitrile (99.8 wt % acetonitrile) is drawn off column 42 as a sidestream via line 50 (This stream may be a vapor or liquid, preferably a vapor), and after cooling in heat exchanger 51 is discharged via line 52 into resin treatment bed 54 where it is treated to produce HPLC grade acetonitrile which is recovered via line 56 in product tank 58.

The temperature for distillation in drying column 32 fluctuates between about 75° F. to 90° F., preferably between 78° F. to 88° F. The typical distillation temperature in the product column is between about 250° F. to 260° F., preferably 255° F. to 258° F.

In a preferred embodiment of the process of the present invention, the following control scheme (not illustrated) may be implemented. The light ends column bottoms temperature is controlled by cascading its control to the feed flow control. The light ends column bottoms temperature control target is set by an equation relating it to the column bottoms pressure. The reboiler steam flow controls the side draw pressure. The side stream vapor flow to the azeotropic condenser is used to control the level in the Digester. The cooling tower water flow to the condenser is used to control the overhead temperature. Then, the overhead temperature target is varied to maintain the light end column temperature profile for ensuring constant composition in the upper section of this column. The light ends Bottoms Level is controlled by the Bottoms blowdown flow. Such a control scheme, in conjunction with the solvent water addition, ensures a more steady composition of all three streams leaving the light ends column.

Once the liquid level has been established in the Azeotrope Condenser Receiver, feed to the Digester can be started. The rate of caustic addition is controlled to ensure that very little acrylonitrile enters the drying column feed. The caustic addition reflects the lower acrylonitrile coming forward with the solvent water addition. The drying column feed is manually fixed flow based upon desired production rates. All other column feed rates are ultimately determined by the drying column fixed feed. The pressure drop in the drying column is controlled by varying the reboiler steam flow. Reflux flow controls the level in the reflux drum. The bottoms level is controlled with the drying column bottoms blowdown. The drying column bottoms temperature is controlled with the product column feed flow. Just as in the light ends column, this control scheme ensures a more steady composition of the two streams leaving the drying column. Cascading the drying column pressure drop with the steam flow keeps loading constant as described for the light ends column.

The product column bottoms level is controlled by adjusting the product column side stream flow. The product column bottoms flow is a manually set fixed flow. The reboiler steam is fixed input as well. Reflux flow controls the tray temperature in the product column. Vapor recycle is fixed as well. The product column liquid recycle split between the light ends column and drying column is targeted by the amount of oxazole present in the recycle. It has been further discovered that changing the proportion of product column liquid recycle going to the light ends column from 30% to 10% present substantial economic advantage to the acetonitrile recovery process. This means the amount of product column recycle going to only the drying column increases from 70% to 90%. With process modeling as well as the plant data, the increased recovery efficiency and processing capacity has been demonstrated.

The following Examples set forth below are illustrative of the practice of the present invention.

EXAMPLE 1

With a light ends column feed of about 12 gpm, the light ends column side stream was showing a typical acrylonitrile concentration in the light ends column side stream vapor composition of about 240 ppm. Within half an hour of adding the solvent water on the top tray without altering or making any changes to the light ends column set points; the acrylonitrile concentration in the light ends column side draw vapor dropped to about 40 ppm. This did give a reason to alter the caustic consumption in digetser from about 120 inches of caustic/shift to about 30 inches of caustic per shift. Even with such a drastic reduction in caustic consumption, the product column side stream acrylonitrile content has decreased from about 3 ppm to below the detectable limit of 100 parts per billion.

In a typical acetonitrile purification unit operation, an acetonitrile product column is operating with a product column liquid overhead reflux flow of 6 gpm. Instead of recycling approximately 1.8 gpm back to the light ends column if we do recycle only 0.6 gpm, the light ends column does not have to reprocess the 1.2 gpm which was about 10% of the light ends column feed of 12 gpm in the above quoted Example 1. This does download the light ends column by about 10% and increases the recovery efficiency and reduces the energy consumption in the overall process.

What we claim as our invention is:

1. A process for the purification of crude acetonitrile containing acrylonitrile as an impurity comprising feeding crude acetonitrile containing acrylonitrile as an impurity and water in addition to the water present in the crude acetonitrile into the upper portion of a distillation column, distilling the crude acetonitrile in the presence of the added water for a time sufficient to allow substantially all of the acrylonitrile present in the crude acetonitrile to be vaporized in the presence of the added water and removed in an overhead stream exiting from the distillation column and recovering the crude acetonitrile substantially free of acrylonitrile from the lower portion of the distillation column.

2. The process of claim 1 wherein the water is fed to the distillation column above the point where the crude acetonitrile enters the distillation column.

3. The process of claim 2 wherein the distillation tower is equipped with trays and the water is fed into the distillation column at a point above the highest tray present in the column.

4. The process of claim 1 wherein the distillation temperature is between about 140° F. to 160° F.

5. The process for the manufacture of HPLC grade acetonitrile comprising (1) feeding (i) crude acetonitrile containing acrylonitrile as an impurity and (ii) water in addition to the water present in the crude acetonitrile into the upper portion of a first distillation column affixed with a first overhead reflux loop at a first pressure of at least 1 atmosphere and distilling the crude acetonitrile in the presence of the added water for a time sufficient to allow substantially all of the acrylonitrile impurity to be absorbed by the added water and removed along with HCN impurity present in the crude acetonitrile in an overhead stream exiting from the first distillation column producing a first acetonitrile/water azeotrope substantially free of acrylonitrile impurity and a first bottom product containing water; (2) distilling the first azeotrope in a second distillation column affixed with a second overhead reflux loop at a second pressure less than 1 atmosphere to separate the first azeotrope into a second bottoms product containing water and a second acetonitrile/water azeotrope having a greater acetonitrile concentration than the first azeotrope, (3) distilling the second aetonitrile/water azeotrope in a third distillation column affixed with a third overhead reflux loop at a third pressure above 1 atmosphere to produce a third acetonitrile/water azeotrope containing substantially all of the water from the second azeotrope, a third bottoms product comprising acetonitrile and heavy organics, and a side stream comprising highly pure acetonitrile, and (4) passing the highly pure acetonitrile side stream through an acidic ion exchange resin to further purify said highly pure acetonitrile producing HPLC grade acetonitrile wherein the reflux ratios in Steps 1, 2 and 3 are kept at greater than 2.7 to 1, greater than 2.2 to 1 and greater than 3.0 to 1, respectively.

6. The process of claim 5 wherein the reflux ratio in step 1 is between about 4.4 to 1.

7. The process of claim 6 wherein the reflux ratio in step 2 is between about 4.5 to 1.

8. The process of claim 7 wherein the reflux ratio in step 3 is maintained between about 8.0 to 1.

9. The process of claim 5 wherein the acidic ion exchange resin is selected to include a strong acid incorporating sulfuric acid functional groups.

10. The process of claim 5 wherein the acidic ion exchange resin is selected to include weak acid resin incorporating carboxylic acid functional groups.

11. The process of claim 5 further comprising distilling the purified acetonitrile recovered from the acidic ion exchange resin.

12. The process of claim 11 wherein the reflux ratio in step 1 is between about 4.4 to 1.

13. The process of claim 12 wherein the reflux ratio in step 2 is between about 4.5 to 1.

14. The process of claim 13 wherein the reflux ratio in step 3 is maintained between about 8 to 1.

15. The process of claim 11 wherein the acidic ion exchange resin is selected to include a strong acid incorporating sulfuric acid functional groups.

16. The process of claim 11 wherein the acidic ion exchange resin is selected to include weak acid resin incorporating carboxylic acid functional groups.

* * * * *

UNITED STATES PATENT AND TRADEMARK OFFICE
CERTIFICATE OF CORRECTION

PATENT NO. : 6,326,508 B1
DATED : December 4, 2001
INVENTOR(S) : Sanjay P. Godbole et al.

It is certified that error appears in the above-identified patent and that said Letters Patent is hereby corrected as shown below:

Column 4,
Line 24, "the second azeotrope. A" should read -- the second azeotrope, a --.

Signed and Sealed this

Twenty-fourth Day of January, 2006

JON W. DUDAS
*Director of the United States Patent and Trademark Office*